US010564047B2

(12) United States Patent
Duchesne et al.

(10) Patent No.: US 10,564,047 B2
(45) Date of Patent: Feb. 18, 2020

(54) CARBON NANOTUBE-BASED MULTI-SENSOR

(71) Applicant: INTERNATIONAL BUSINESS MACHINES CORPORATION, Armonk, NY (US)

(72) Inventors: Eric Duchesne, Quebec (CA); Dominique Drouin, Quebec (CA); Hélène Frémont, Léognan (FR); Simon Landry, Granby (CA); Aurore F. M. E. Quelennec, Argenteuil (FR); Umar Shafique, Quebec (CA); Patrick R. J. Wilson, Onatario (CA)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 387 days.

(21) Appl. No.: 15/434,230

(22) Filed: Feb. 16, 2017

(65) Prior Publication Data

US 2018/0231483 A1    Aug. 16, 2018

(51) Int. Cl.
*G01N 27/12* (2006.01)
*H01L 23/29* (2006.01)
*H01L 23/498* (2006.01)
*H01L 23/00* (2006.01)
*G01L 1/22* (2006.01)
*G01K 7/16* (2006.01)

(52) U.S. Cl.
CPC .............. *G01K 7/16* (2013.01); *H01L 24/16* (2013.01); *H01L 2224/16225* (2013.01)

(58) Field of Classification Search
CPC ...... G01K 7/16; G01K 7/226; G01K 2211/00; H01L 24/16; H01L 23/49811; H01L 23/293; H01L 2224/16225; G01L 1/225; G01N 27/127
See application file for complete search history.

(56) References Cited

U.S. PATENT DOCUMENTS

| 7,741,834 | B2 * | 6/2010 | Dang ................ G01R 31/2812 324/762.02 |
| 9,028,142 | B2 | 5/2015 | Raravikar et al. |
| 9,068,283 | B2 | 6/2015 | Biris et al. |
| 9,080,907 | B2 | 7/2015 | Haneef et al. |
| 9,267,853 | B2 | 2/2016 | Fernandes et al. |
| 2007/0134599 | A1 * | 6/2007 | Raravikar ........... B81C 1/00206 430/325 |
| 2007/0222472 | A1 * | 9/2007 | Raravikar .............. B82Y 10/00 73/774 |

(Continued)

OTHER PUBLICATIONS

Eric Duchesne, et al., Pending U.S. Appl. No. 15/795,640 entitled "Carbon Nanotube-Based Multi-Sensor," filed with the U.S. Patent and Trademark Office on Oct. 27, 2017.

(Continued)

*Primary Examiner* — Lee E Rodak
(74) *Attorney, Agent, or Firm* — Cantor Colburn LLP; Steven Meyers

(57) ABSTRACT

Carbon nanotube-based multi-sensors for packaging applications and methods to form the carbon nanotube-based multi-sensors are capable of simultaneously measuring at least two measurands including temperature, strain, and humidity via changes in its electrical properties.

3 Claims, 18 Drawing Sheets

(56) References Cited

U.S. PATENT DOCUMENTS

| | | | | |
|---|---|---|---|---|
| 2007/0298525 | A1* | 12/2007 | Raravikar | G01L 1/20 438/14 |
| 2008/0002755 | A1* | 1/2008 | Raravikar | B82Y 15/00 374/100 |
| 2008/0191319 | A1* | 8/2008 | Woo | H01L 23/3128 257/622 |
| 2014/0105242 | A1* | 4/2014 | Fernandes | G01J 5/046 374/45 |
| 2016/0322265 | A1* | 11/2016 | Gao | H01L 22/14 |
| 2018/0047644 | A1* | 2/2018 | Davis | H01L 22/14 |

OTHER PUBLICATIONS

List of IBM Patents or Patent Applications Treated As Related; (Appendix P), Date Filed Oct. 27, 2017; 2 pages.

Lee, et al., "Microfabrication and characterization of spray-coated single-wall carbon nanotube film strain gauges," Nanotechnology, vol. 22, (2011) 455301; 6 pages.

Moraes, et al., "Development of Fast Response Humidity Sensors Based on Carbon Nanotubes," Sensordevices 2014: The Fifth International Conference on Sensor Device Technologies and Applications; 4 pages.

Nanjunda, et al., Highly Sensitive Carbon Nanotbues Coated Etched Fiber Bragg Grating Sensor for Humidity Sensing, IEEE Sensors Journal: vol. 14, No. 8, (Aug. 2014); 5 pages.

Quelennec, et al., "Carbon nanotubes-based sensor patent," Combined High Sensitivity Temperature, Humidity and Strain Sensor Based on Carbon Nanotuves for Microelectronic Packaging Applications: Universite de Sherbrooke, (2017); 5 pages.

Xiaowei, et al., "Novel capacitance-type humidity sensor based on multi-wall carbon nanotube/SiO2 composite films," Journal of Semiconductors: vol. 32, No. 3; (Mar. 2011), 5 pages.

* cited by examiner

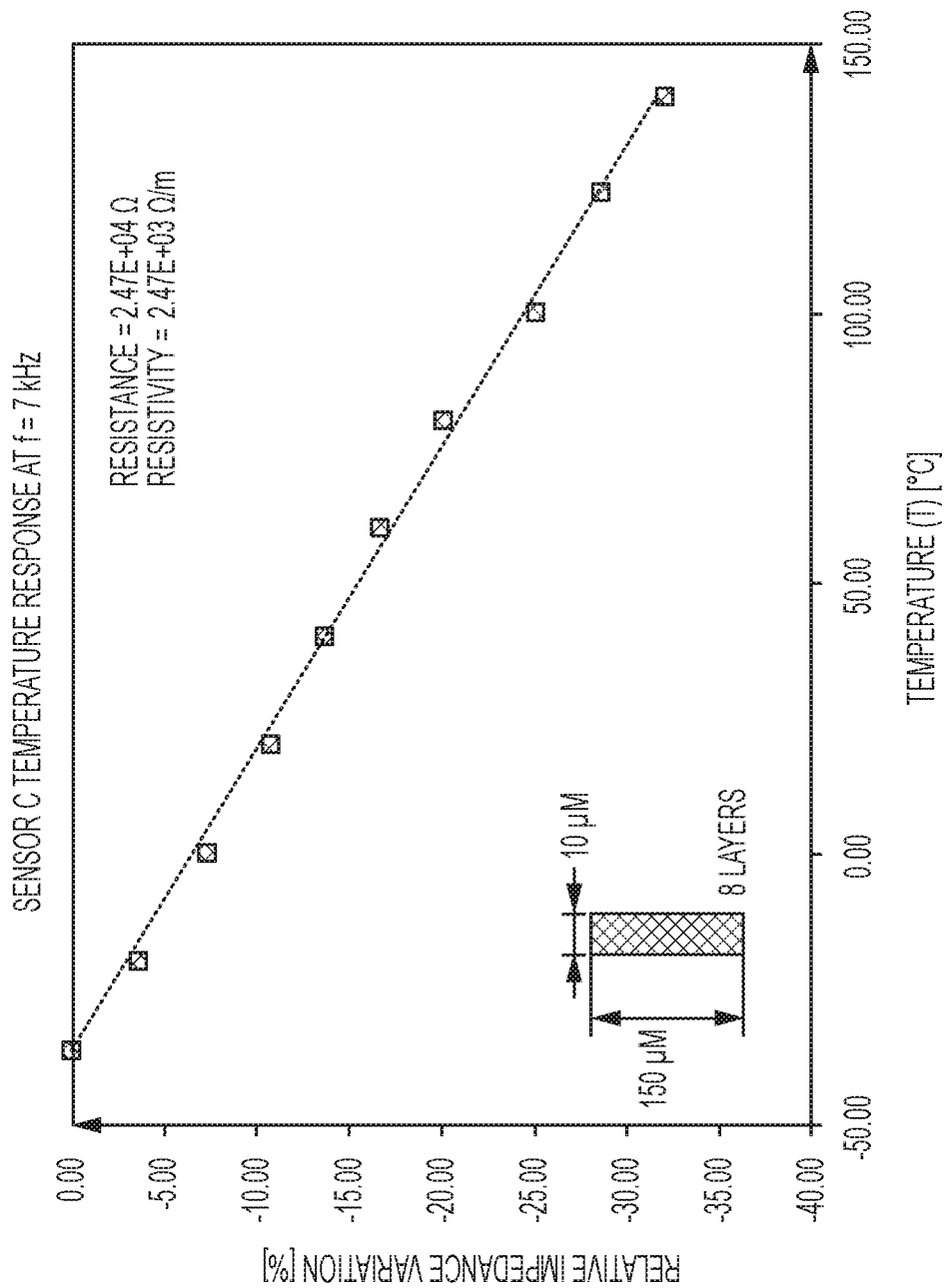

CARBON NANOTUBE-BASED MULTI-SENSOR

BACKGROUND

The present invention relates to carbon nanotube-based multi-sensors, and more particularly, combined high sensitivity strain, temperature and/or humidity multi-sensors based on carbon nanotubes for microelectronic applications.

A chip typically includes integrated circuits formed by front-end-of-line (FEOL) processing and metallization levels of an interconnect structure formed by back-end-of line (BEOL) processing. The chips are packaged in modules and usually not directly mounted on a circuit board. Module packaging provides electrical connectivity between the chip and the circuit board, protection against thermal and mechanical stresses, and protection against environmental corrosion. Solder bumps are commonly utilized to provide mechanical and electrical connections between the last or top metallization level in the chip and the circuit board.

By way of example, C4 (Controlled-Collapse Chip Connection) can be utilized to connect integrated circuit chips to substrates in electronic packages. In particular, C4 is a flip-chip packaging technology in which the interconnections are small solder balls (or bumps or pillars) formed on the chip surface. The top layers of an integrated circuit chip include various wiring levels, separated by insulating layers of dielectric material, that provide input/output (I/O) for the device. In C4 structures, the chip wiring is terminated by a plurality of metal films that form the ball-limiting metallurgy (BLM). The BLM defines the size of the solder bump after reflow, and provides a surface that is wettable by the solder and that reacts with the solder material to provide good adhesion with acceptable reliability under mechanical and thermal stress. In addition, the BLM also serves as a diffusion barrier between the integrated circuit device and the metals in the interconnection.

Well established technologies like silicon-based piezo resistive or foil based as strain sensors, aluminum oxide-based or polyimide-based as humidity sensors, and transistors or diodes as temperature sensors are commonly used. However, disadvantages like size, low sensitivity, lack of positioning flexibility and/or incompatibility with existing micro-electronic processes limit their use especially for in-situ measurements in micro-electronic modules.

SUMMARY OF THE INVENTION

The present invention is directed to a carbon nanotube-based multi-sensors and methods of forming the carbon nanotube-based multi-sensor for a chip package.

In one or more embodiments, a method of forming a carbon nanotube-based multi-sensor for a chip package is provided. In this method, a layer of carbon nanotube dispersion is spray coated onto a surface of a chip and/or a laminate and dried. The process is repeated form a multilayer of a carbon nanotube mesh. The carbon nanotube mesh is patterned to form a carbon nanotube mesh pattern and encapsulated with a polymer matrix to form a composite material leaving exposed terminal ends. Metal electrodes are attached to the exposed terminal ends of the carbon nanotube mesh and the metal electrodes are connected to a voltage source.

In one or more embodiments, a carbon nanotube-based multi-sensor for independently measuring temperature, strain, and relative humidity responses in a chip package includes a laminate substrate having a plurality of electrical circuits disposed therein, and a chip having a first surface mounted on the laminate substrate and electrically connected to electrical circuits disposed in laminate substrate. An underfill material is disposed between the chip and the laminate substrate, wherein a selected one or both of the chip and the laminate substrate further comprises a passivation layer thereon. The carbon nanotube-based multi-sensor is disposed on the passivation layer and includes a carbon nanotube mesh pattern encapsulated in a moisture permeable polymer matrix with terminal ends exposed. Electrodes are coupled to the terminal ends. The carbon nanotube-based multi-sensor further includes a processor for treating a signal generated from the carbon nanotube-based multi-sensors when a voltage is applied to the electrodes. The processor is configured to independently measure a variation in an electrical property at a defined frequency as a function of the temperature, strain and relative humidity.

In one or more embodiments, a method for measuring temperature, strain and/or humidity in a microelectronic package includes providing one or more carbon nanotube-based multi-sensors within the microelectronic package. Each of the one or more carbon nanotube-based multi-sensors includes a moisture permeable polymer encapsulated carbon nanotube mesh pattern including exposed terminal ends electrically coupled to electrodes, wherein the carbon nanotube mesh pattern comprises a meander pattern or a patch pattern. A voltage is applied to the electrodes and impedance variation is measured as a function of temperature, strain, and/or humidity responses at a frequency.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 27 graphically illustrates relative impedance variation as a function of temperature at a frequency of 7 kHz for the patch patterned carbon nanotube-based multi-sensor C of FIG. 23.

Figure 1:
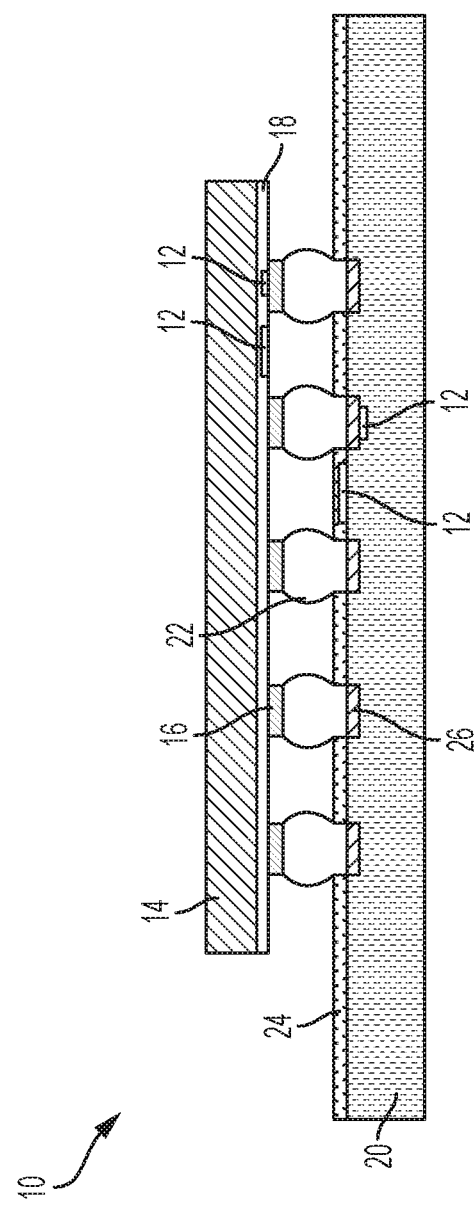
FIG. 1 schematically illustrates a cross sectional view of an exemplary integrated circuit package assembly in accordance with one or more embodiments of the present invention.

It will be appreciated that for simplicity and clarity of illustration, elements shown in the drawings have not necessarily been drawn to scale. For example, the dimensions of some of the elements may be exaggerated relative to other elements for purpose of clarity.

DETAILED DESCRIPTION

In high-performance semiconductors, the back-end-of-line (BEOL) interconnect pitch has been shrinking for decades following Moore's law. Steady advances in very-large-scale integration (VLSI) technology for both digital and analog devices could never have been achieved without overcoming various reliability risks in IC chips as well as packages. In many cases, such challenges do not reside solely in a package or an IC chip. Rather, the interaction between the package and the IC chip is important as the coefficients of thermal expansion (CTEs) of the silicon die and package materials, such as plastic molding compounds or organic substrates, can differ significantly. This CTE mismatch induces thermo-mechanical stresses at the interfaces during thermal excursions, which can compromise the chip's structural integrity. The influence of the package-induced stress on the chip is called chip-package interaction (CPI), and it plays a key role in overall product reliability. Similarly, moisture absorption by the different materials used can cause delamination and/or corrosion, which can also affect overall product reliability.

The present invention is generally directed to multi-sensors based on carbon nanotubes integrated into a package and capable of independently measuring temperature, strain and humidity using multiple excitation signal frequencies and a signal treatment. The carbon nanotube-based multi-sensors are formed on a chip and/or a laminate layer of a package. As will be described herein, in one or more embodiments, each carbon nanotube-based multi-sensor can be configured to independently measure strain, temperature and humidity using three excitation single frequencies and a signal treatment. In other embodiments, multiple carbon nanotube-based multi-sensor can be disposed on the chip and/or laminate as will be described below, wherein each carbon nanotube-based multi-sensor can also be configured to specifically measure either temperature, humidity or strain at a single pre-defined frequency. In the various embodiments, the carbon nanotube-based multi-sensors are formed of randomly oriented spray coated carbon nanotubes that form a carbon nanotube mesh pattern configured to independently provide temperature, humidity and strain measurements within specific independent ranges of frequencies or at a single predefined frequency. Those frequency ranges as well as selection of a single predefined frequency are intrinsic characteristics of each carbon nanotube-based sensor and depend on their base resistance and resistivity which can be adjusted by modifying the sensor geometry characteristics (e.g., line length, width, thickness and pattern). The carbon-based nanotube multi-sensors can be located on the laminate, the chip, in between bumps or under the BLM in high stress regions. The carbon nanotubes can be single wall carbon nanotubes (SWCNT) or multi-wall carbon nanotubes (MWCNT). Still further, suitable carbon nanotubes can be metallic and/or semiconducting with or without chemical functionalization.

Advantageously, integration of the carbon based nanotube multi-sensors in microelectronic packaging applications is compatible with existing chip, laminate, and fabrication processes as well as being compatible with module bond, assembly and testing (BAT) materials and processes. As such, the carbon nanotube based multi-sensors are capable of measuring a full range of temperature, strain and humidity associated with module fabrication, electrical test, reliability stressing, and operation.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

As used herein, the articles "a" and "an" preceding an element or component are intended to be nonrestrictive regarding the number of instances (i.e. occurrences) of the element or component. Therefore, "a" or "an" should be read to include one or at least one, and the singular word form of the element or component also includes the plural unless the number is obviously meant to be singular.

As used herein, the terms "invention" or "present invention" are non-limiting terms and not intended to refer to any single aspect of the particular invention but encompass all possible aspects as described in the specification and the claims.

As used herein, the term "about" modifying the quantity of an ingredient, component, or reactant of the invention employed refers to variation in the numerical quantity that can occur, for example, through typical measuring and liquid handling procedures used for making concentrates or solutions. Furthermore, variation can occur from inadvertent error in measuring procedures, differences in the manufacture, source, or purity of the ingredients employed to make the compositions or carry out the methods, and the like. In one aspect, the term "about" means within 10% of the reported numerical value. In another aspect, the term "about" means within 5% of the reported numerical value. Yet, in another aspect, the term "about" means within 10, 9, 8, 7, 6, 5, 4, 3, 2, or 1% of the reported numerical value.

It will also be understood that when an element, such as a layer, region, or substrate is referred to as being "on" or "over" another element, it can be directly on the other element or intervening elements may also be present. In contrast, when an element is referred to as being "directly on" or "directly over" another element, there are no intervening elements present, and the element is in contact with another element.

FIG. 1 schematically illustrates a partial cross-sectional view of an exemplary integrated circuit (IC) package assembly 10 including one or more carbon nanotube multi-sensors 12 in accordance with the present invention. The IC package assembly 10 can include a chip 14 having a plurality of (e.g., two or more) BLM 16 surface mounted onto a passivation layer 18 on the chip 14. The chip 14 can be attached to the package substrate 20 according to a variety of suitable configurations including, a flip-chip configuration as depicted, or other configurations as can be desired for different applications. Using the flip-chip configuration as an example, the active side of the chip 14 is attached to a surface of the package substrate 20, e.g., a laminate, a printed circuit board, or the like, using interconnect structures 22 such as solder bumps or copper (Cu) pillars, as shown. The active side of the chip 14 may have one or more transistor devices formed thereon and may be, include, or be a part of a processor, memory, or application specific integrated circuit (ASIC) in some embodiments. As shown, the carbon-based nanotube multi-sensors can be located on the laminate, the chip, in between bumps or under the BLM in high stress regions.

Figure 2:
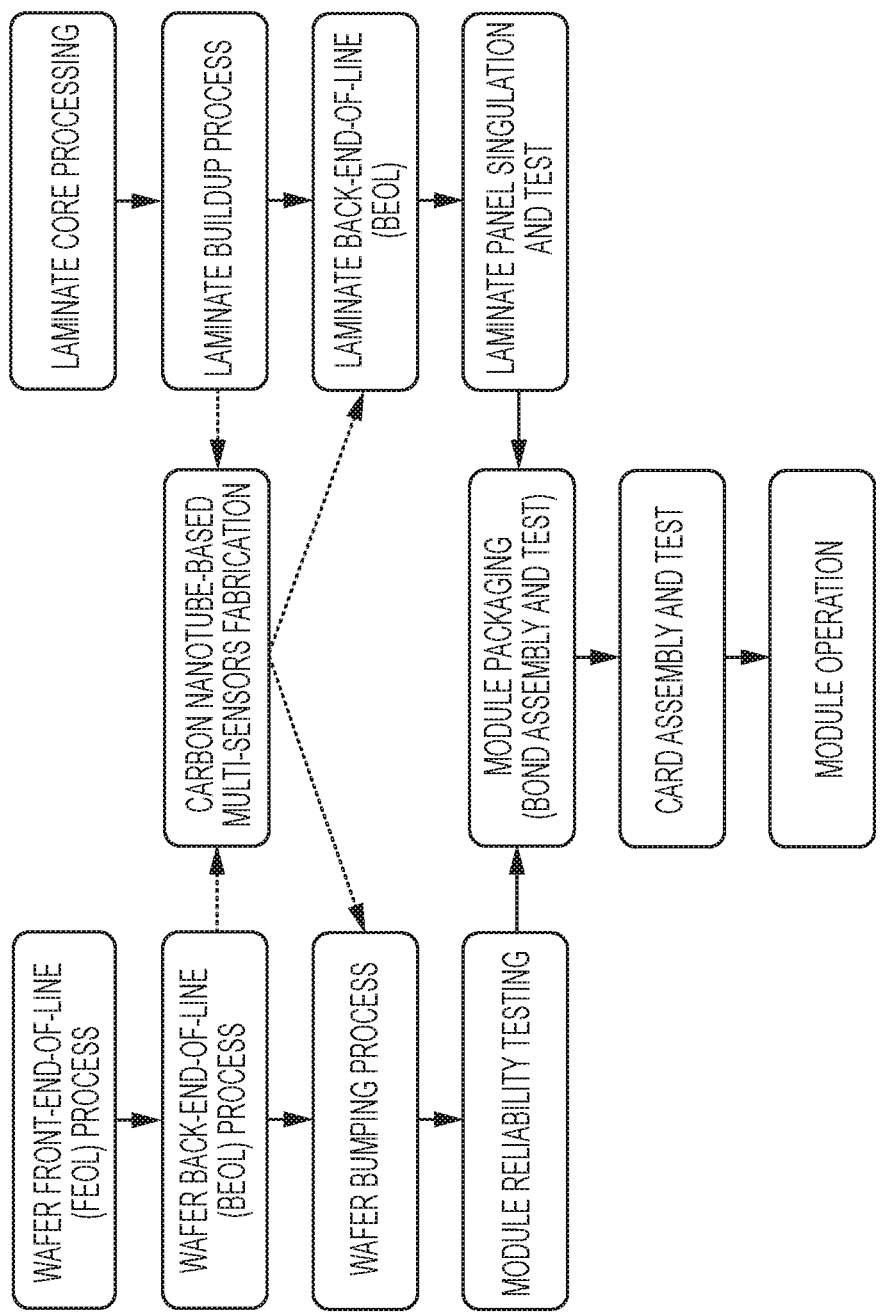
FIG. 2 is a flowchart illustrating a process for packaging a chip including carbon based multi-sensors for independently measuring strain, temperature, and/or humidity at a location within the chip package in accordance to one or more embodiments of the present invention.

Referring now to FIG. 2, the generally process flow for integrating the carbon nanotube-based multi-sensors into existing packaging processes is shown. The carbon nanotube-based multi-sensors can be integrated during chip assembly on a wafer generally shown on the left side and/or be integrated during laminate assembly (or printed circuit board assembly) generally shown on the right side. With regard to the chip assembly, the carbon nanotube-based multi-sensor(s) can be fabricated prior to wafer bumping. With regard to laminate fabrication, the carbon nanotube-based multi-sensors can be fabricated prior to and/or during laminate back end of line processing. In one or more embodiments, the carbon nanotube-based multi-sensors are fabricated on passivation layers of the respective chip or laminate assembly. As previously noted, the location is not intended to be limited and can be positions on the chip, the laminate, aligned with the interconnect structure or between interconnect structures, thereby providing wide latitude for temperatures, strain, and humidity measurements. As such, the carbon nanotube based multi-sensors are capable of measuring a full range of temperature, strain and humidity associated with module fabrication, electrical test, reliability stressing, and operation including, but not limited to, module reliability testing, laminate panel singulation and testing, module packaging (BAT), card assembly and testing and during module operation.

FIGS. 3-13 depict cross sectional views for fabricating the carbon nanotube-based multi-sensor 100 in accordance with one or more embodiments of the invention. FIG. 14 depicts an exploded perspective view of the carbon nanotube-based multi-sensor 100 as fabricated.

Figure 3:
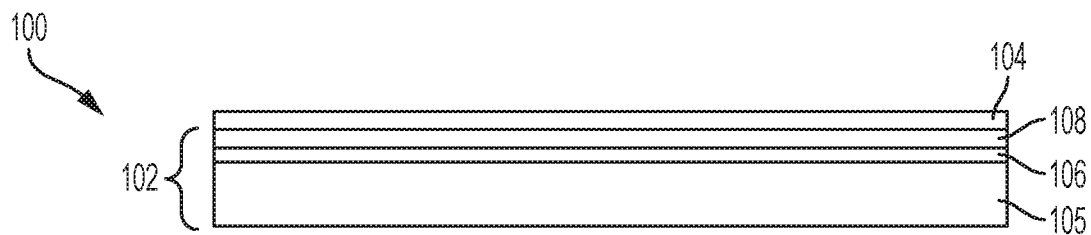
FIG. 3 schematically illustrates a cross-sectional view of a substrate for chip assembly including a passivation layer thereon in accordance to one or more embodiments of the present invention.

As shown in FIG. 3, the fabrication process begins with deposition of a passivation layer 104 onto a substrate 102. The substrate 102 includes a silicon wafer integrated circuits after front-end-of-line (FEOL) processing or a laminate panel after core processing 105 with metallization layers 106 and isolation layer 108. The isolation layer 108 can be but is not limited to silicon oxide (SiO2), silicon nitride (SiN) or a dielectric polymer based film. The substrate can also include a metal bond pad (e.g., copper, aluminum) formed at an uppermost metallization level (not shown) that serves to provide an external connection to the active devices formed in the substrate through various levels of interconnect structures there between (not shown). In that case, openings in the passivation layer 104 can be lithographically patterned to allow electrical connection to the substrate metal bond pads (also not shown). The passivation layer 104 can be a dielectric film with useful mechanical properties that make it suitable as a stress buffer passivation layer that improves device reliability by eliminating stresses introduced during packaging operations. Suitable materials for forming the passivation layer 104 include, but are not limited to, photosensitive polyimide (PSPI), benzocyclobutene (BCB), silicon nitride (SiN), silicon oxide (SiO2) or the like. Optionally, a surface treatment pre-processing like plasma etch (e.g. argon and oxygen) or an organosilane-type adhesion promoter or the like can be used prior to deposition of the passivation layer 104 to provide improved adhesion as may be desired in some applications. The passivation layer can be a single layer or multi-layered and is lithographically patterned to provide via openings generally corresponding to the metal pads.

Figure 4:
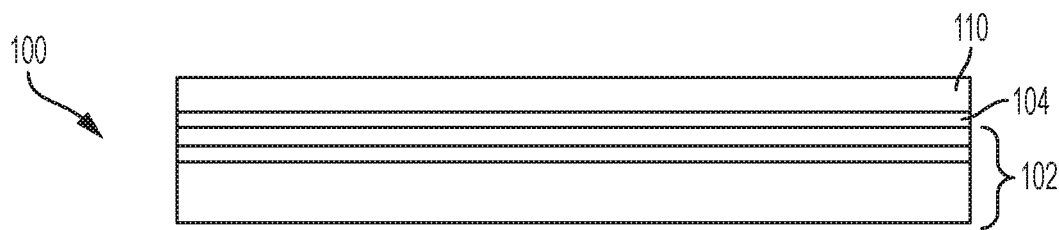
FIG. 4 schematically illustrates a cross-sectional view of the chip assembly of FIG. 3 subsequent to deposition of a conductor layer on the passivation layer thereon in accordance to one or more embodiments of the present invention.
Figure 5:
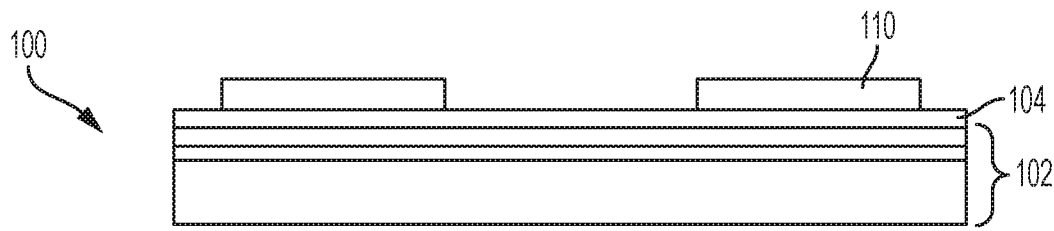
FIG. 5 schematically illustrates a cross-sectional view of the chip assembly of FIG. 4 subsequent to patterning the conductor layer in accordance to one or more embodiments of the present invention.

In FIGS. 4-5, BLM connector lines are formed of a metal conductor such as aluminum, copper or the like. As shown in FIG. 4, the metal conductor is deposited onto the passivation layer 104. In FIG. 5, metal conductor layer 110 is then lithographically patterned and etched to form a desired pattern so as to subsequently provide BLM to sensor connection upon fabrication of the sensor 100.

Figure 6:
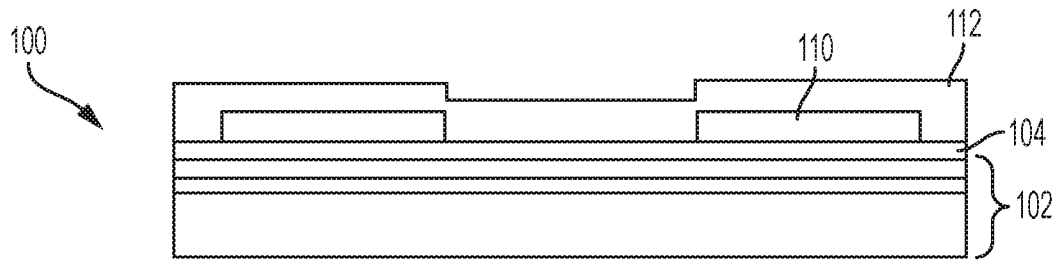
FIG. 6 schematically illustrates a cross-sectional view of the chip assembly of FIG. 5 subsequent to spray deposition of a carbon nanotube solution to form a carbon nanotube mesh in accordance to one or more embodiments of the present invention.

In FIG. 6, an isotropic dispersion of carbon nanotubes in a non-aqueous solvent such as N-methyl-2-pyrrolidone (NMP) is spray coated multiple times onto the passivation layer to form an interlaced mesh of carbon nanotubes 112 across the surface of the passivation layer and the metal conductor 110. During each spray coating pass, the substrate is heated to remove the organic solvent. The spray coated carbon nanotubes as deposited are randomly oriented (i.e., isotropic) and non-agglomerated. In one or more embodiments, the thickness of the carbon nanotube mesh 112 can be from about 200 nm to about 900 nm.

By way of example, short multi-walled carbon nanotubes functionalized with carboxyl groups (s-MWCNT-COOH) previously treated by an oxygen plasma can be dispersed in NMP with a ratio of 1 milligram (mg)/10 milliliter (mL) using ultrasound for 60 minutes (min). The resulting carbon nanotube solution can be spray coated onto the polyimide surface at a flow rate of 0.25 mL/min and a head speed of 40 millimeters (mm)/min to cover the surface of the substrate. During spray deposition, the substrate can be placed onto a heated surface, e.g., a hot plate, at, for example, 220° C. so as to evaporate the solvent. Multiple layers are deposited to form the carbon nanotube mesh at the thicknesses described above.

Figure 7:
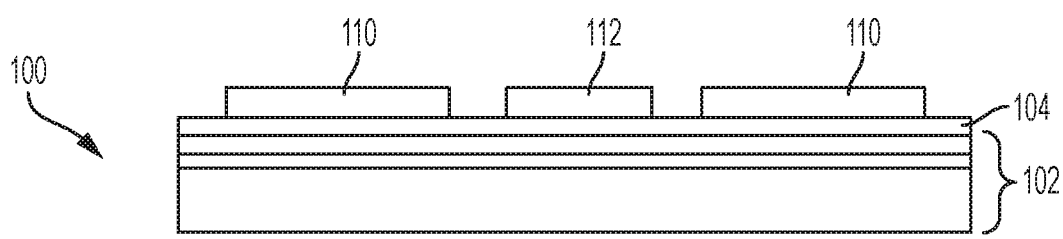
FIG. 7 schematically illustrates a cross-sectional view of the chip assembly of FIG. 6 subsequent to patterning the carbon nanotube based mesh in accordance to one or more embodiments of the present invention.

Referring now to FIG. 7, the carbon nanotube layer 112 is lithographically patterned and etched to define each carbon nanotube based multi-sensor. The lithographic step can include forming a photoresist (organic, inorganic or hybrid) atop the carbon nanotube layer 112. The photoresist can be formed utilizing a deposition process such as, for example, CVD, PECVD, and spin-on coating. Following formation of the photoresist, the photoresist is exposed to a desired pattern of radiation. Next, the exposed photoresist is developed utilizing a conventional resist development process. After the development step, an etching step can be performed to transfer the pattern from the patterned photoresist into the carbon nanotube layer 112. The etching step used in forming the carbon nanotube based pattern can include a dry etching process (including, for example, reactive ion etching, ion beam etching, plasma etching or laser ablation), a wet chemical etching process or any combination thereof. In one or more embodiments, the etching step can be an oxygen based plasma. Following etching, the remaining photoresist is removed and the substrate cleaned to provide a pattern of the carbon nanotube mesh on the passivation layer. As will be discussed in greater detail below, the geometric patterns of carbon nanotubes 112 can generally be described as a meander or as a patch. An exemplary meander pattern is one having a serpentine shape.

Figure 8:
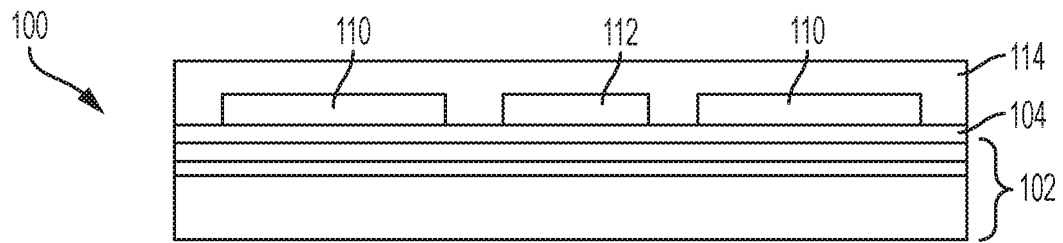
FIG. 8 schematically illustrates a cross-sectional view of the chip assembly of FIG. 7 subsequent to deposition of a moisture permeable polymer matrix in accordance to one or more embodiments of the present invention.

Referring to FIG. 8, the electrodes are formed by first depositing a moisture permeable polymer matrix layer 114, e.g., PSPI, onto the substrate including the patterned carbon nanotubes 112. Alternatively, the polymer matrix can be impermeable, wherein the resulting sensors are configured to measure strain and temperature.

Figure 9:
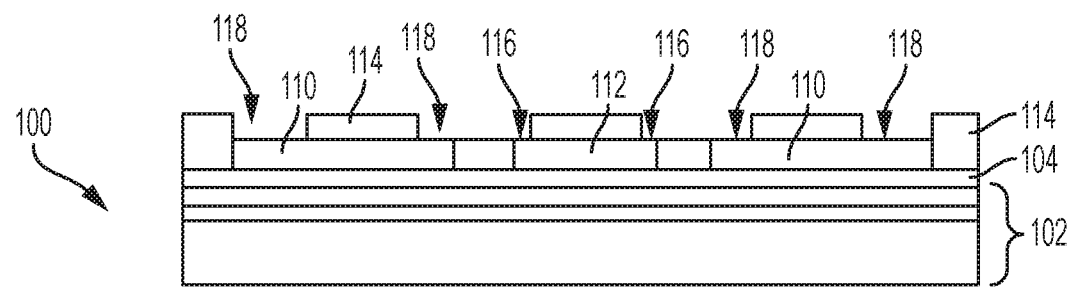
FIG. 9 schematically illustrates a cross-sectional view of the chip assembly of FIG. 8 subsequent to patterning the moisture permeable polymer matrix in accordance to one or more embodiments of the present invention.

In FIG. 9, the permeable polymer matrix 114 is lithographically patterned to expose terminal ends 116 of the patterned carbon nanotubes 112 while encapsulating and protecting the remaining pattern of carbon nanotubes there between. In a similar manner, portions 118 of the conductor layer 110 are exposed while protecting the remaining pattern of metal conductor.

Figure 10:
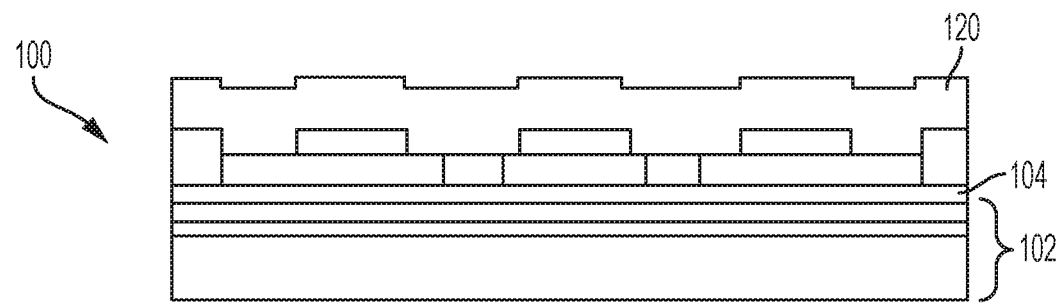
FIG. 10 schematically illustrates a cross-sectional view of the chip assembly of FIG. 9 subsequent to deposition of a metal layer in accordance to one or more embodiments of the present invention.
Figure 11:
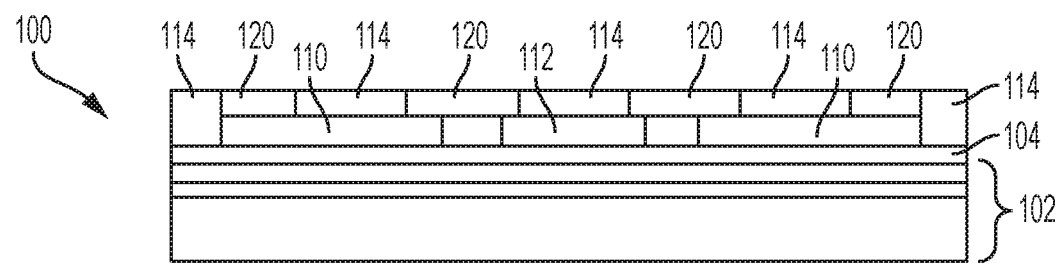
FIG. 11 schematically illustrates a cross-sectional view of the chip assembly of FIG. 10 subsequent to patterning of the metal layer in accordance to one or more embodiments of the present invention.

In FIGS. 10 and 11, electrodes 120 are subsequently deposited onto the substrate including the terminal ends 116, 118 to provide an electrical connection to the patterned carbon nanotubes 112 and connector lines 110. Suitable metals for electrodes include, without limitation, any carbon nanotube compatible metal such as Titanium (Ti) and Titanium-Tungsten (TiW).

Figure 12:
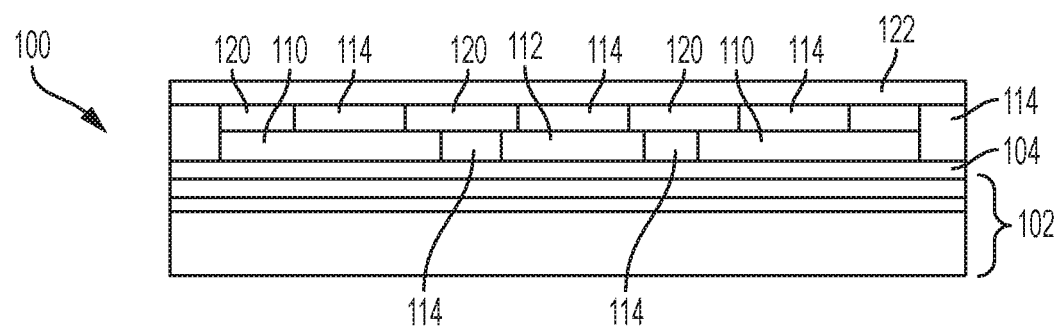
FIG. 12 schematically illustrates a cross-sectional view of the chip assembly of FIG. 11 subsequent to deposition of a top passivation layer in accordance to one or more embodiments of the present invention.
Figure 13:
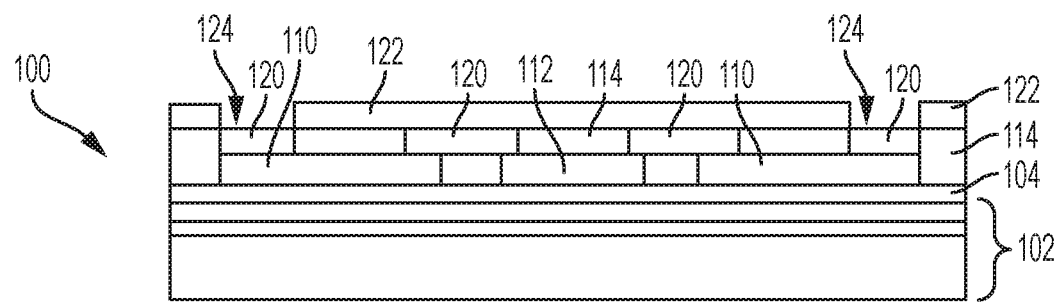
FIG. 13 schematically illustrates a cross-sectional view of the chip assembly of FIG. 13 subsequent to patterning the top passivation layer in accordance to one or more embodiments of the present invention.
Figure 14:
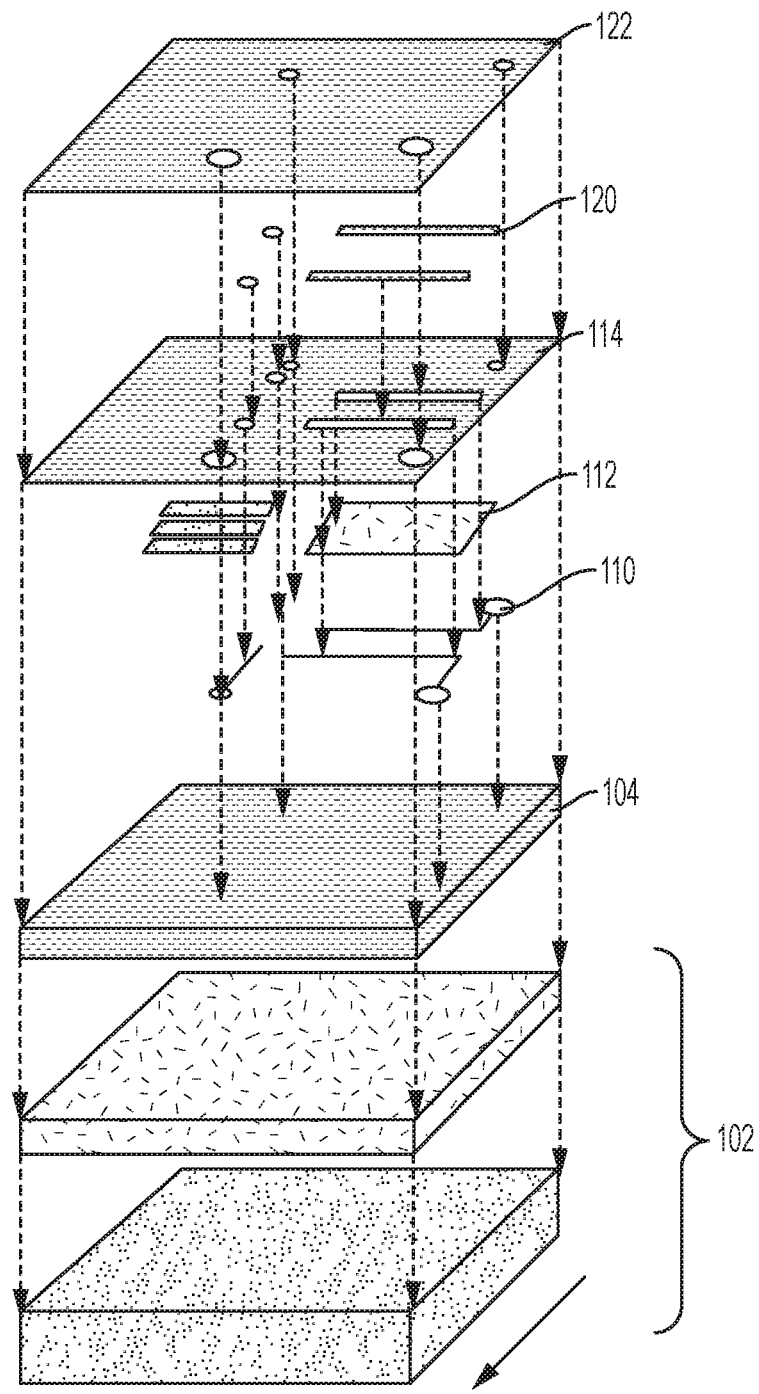
FIG. 14 is an exploded perspective view of the chip assembly of FIG. 13 in accordance to one or more embodiments of the present invention.

In FIGS. 12 and 13, a top passivation layer 122 is deposited over the electrodes 120. Openings 124 are lithographically patterned to form electrical connection paths to the active reading device outside the substrate via interconnections structures (e.g. C4 BLM's). Alternatively, the top passivation 122 can be formed without openings 124 if the sensor is electrically connected to the active reading device through the substrate 102 via metal bond pads (e.g., copper, aluminum) formed at an uppermost metallization level and through various levels of interconnect structures there between (not shown).

FIG. 14 provides an exploded perspective view of the carbon nanotube sensor 100. As shown, the sensor includes a substrate 102, which can include metallization layers and isolation layer as previously described. A bottom, i.e., base, passivation layer 104 is disposed on the substrate 102. The BLM to the carbon nanotube exposed sensor end connections are provided by the aluminum patterned lines 110 and the Titanium-Tungsten electrode 120. A meander pattern, e.g., a serpentine pattern, as well as a patch pattern of the carbon nanotubes mesh is depicted at layer 112. The sensor 100 further includes the patterned moisture permeable polymer matrix layer 114 and the top passivation layer 122 including openings for electrically connecting an external reading device to the sensors.

Once positioned on a chip or a laminate, each carbon nanotube-based multi-sensor can be electrically coupled by means of a sinusoidal alternating current (AC) voltage applied to each sensor's electrode pair. After baseline conditions are established, the resulting excitation signals are treated at two or more frequencies (f) by Fourier analysis. From this signal treatment, the variation of impedance as a function of strain, temperature or relative humidity can independently be determined at a given frequency. Because a direct correlation exists between impedance of a carbon nanotube-polymer composite material and changes in the electrical properties as a function of strain, temperature or humidity, the carbon nanotube-based multi-sensors are indicative of changes in one or more of the parameters of strain, humidity and temperature experienced by the structure depending upon how each sensor was optimized. In terms of dynamic structures, such monitoring could occur during module BAT, reliability stressing, and end application.

Figure 15:
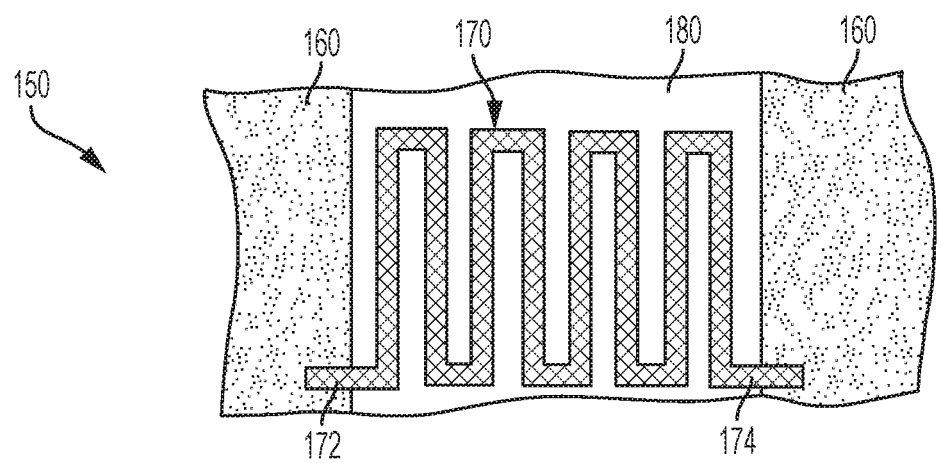
FIG. 15 is a top down view of an exemplary serpentine-patterned carbon nanotube-based micro-sensor including electrodes coupled to terminal ends of the serpentine shaped carbon nanotube-based micro-sensor in accordance to one or more embodiments of the present invention.
Figure 16:
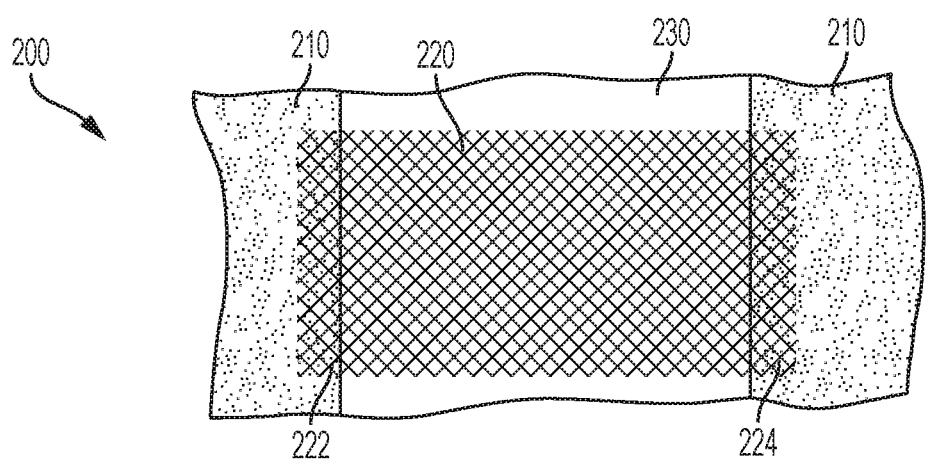
FIG. 16 is a top down view of an exemplary patch-shaped carbon nanotube-based micro-sensor including electrodes coupled to terminal ends of the serpentine shaped carbon nanotube-based micro-sensor in accordance to one or more embodiments of the present invention.

FIGS. 15 and 16 are illustrative of two but not exclusive carbon nanotube-based multi-sensor patterns 150 and 200 (serpentine and patch), respectively, that can be configured to independently measure strain, temperature and humidity using three excitation single frequencies and a signal treatment. Each carbon nanotube-based multi-sensor can also be configured to specifically measure either temperature, humidity or strain at a pre-defined frequency. Those frequency ranges are intrinsic characteristics of each carbon nanotube-based sensor and depend on their base resistance and resistivity which can be adjusted by modifying the sensor geometry characteristics (e.g., line length, width, thickness and pattern). The carbon nanotube-based multi-sensor 150 includes a serpentine-shaped carbon nanotube patterns 170 including terminal ends 172 and 174. With the exception of terminal ends, the serpentine-shaped carbon nanotube patterns is fully encapsulated in a moisture permeable polymer matrix 180 to form a composite sensing material. Electrodes 160 are electrically connected to the terminal ends. The carbon nanotube-based multi-sensor 200 includes a patch-shaped carbon nanotube patterns 220 including terminal ends 222 and 224. With the exception of terminal ends, the patch-shaped carbon nanotube pattern is fully encapsulated in a permeable polymer matrix 230 to form a composite sensing material. Electrodes 210 are electrically connected to the terminal ends.

Temperature, strain and humidity can be monitored by measuring the change in the carbon nanotube-based multi-sensor electrical properties such as impedance at different excitation frequencies.

Figure 17:
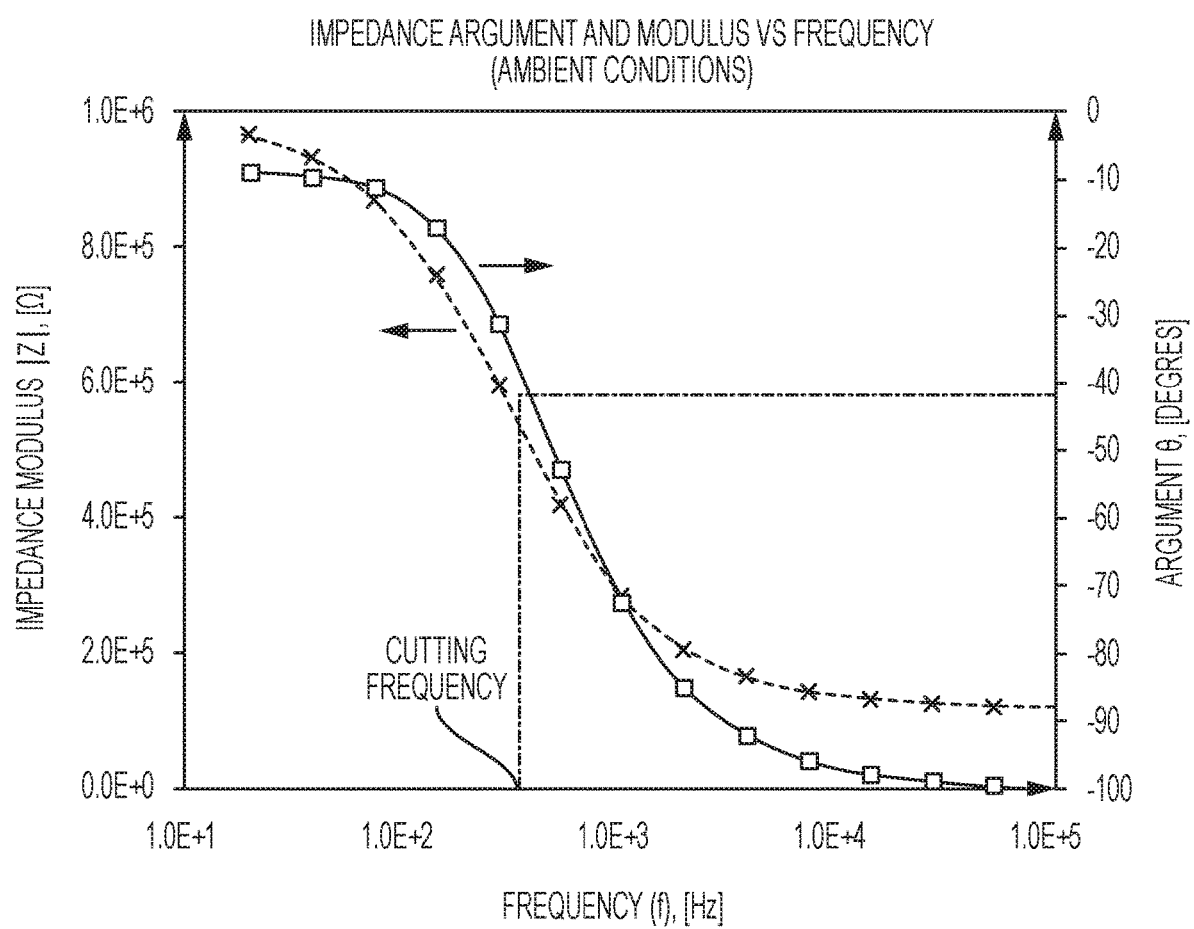
FIG. 17 graphically illustrates impedance (modulus and argument) as a function of excitation voltage frequency at ambient base conditions (25° C., 45% RH) for a carbon nanotube-based multi-sensor in accordance with one or more embodiments of the present invention.

FIG. 17 shows graphically the typical carbon nanotube-based multi-sensor impedance (modulus and argument) in accordance with the present invention as a function of excitation voltage frequency at ambient base conditions (25° C., 45% RH). As shown, the sensor behaves as a low pass filter by cutting certain frequencies. The cut-off frequency is generally defined as a boundary in the system's frequency response at which energy flowing through the multi-sensor begins to be reduced (attenuated or reflected) rather than passing through.

Figure 18:
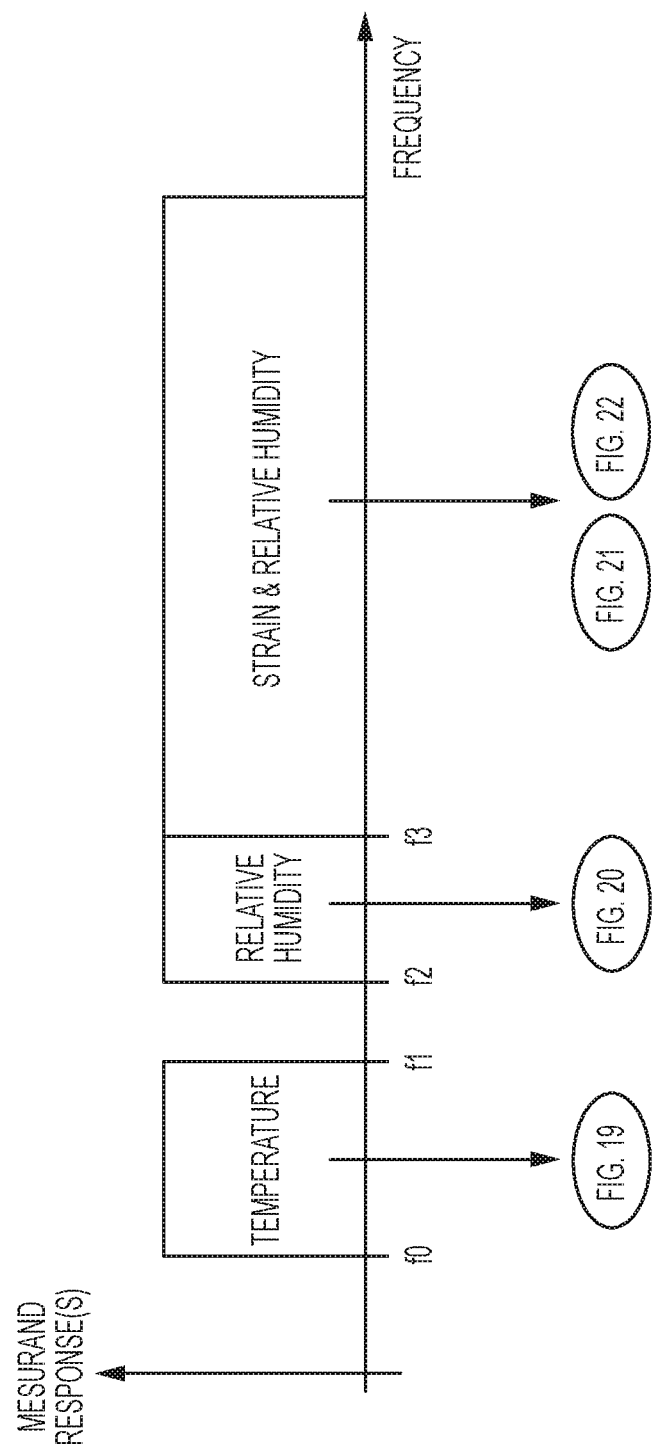
FIG. 18 graphically illustrates frequency ranges for several measurands for an exemplary serpentine pattern carbon nanotube-based multi-sensor in accordance with one or more embodiments of the present invention.

As shown in FIG. 18, in one more embodiments, fixed geometry carbon nanotube-based multi-sensors can be configured to measure the temperature, humidity and strain responses at different and independent frequency ranges, wherein the particular frequency ranges can vary depending on the sensor geometry characteristics (e.g., line length, width, thickness and pattern). For example, the carbon nanotube based multi-sensor can be configured to monitor temperature at a relatively low excitation frequency range of f0 to f1; relative humidity can be monitored at a mid-level excitation frequency range of f2 to f3; and strain can be monitored at relatively high excitation frequencies greater than f3. FIGS. 19-22 graphically illustrate relative impedance variation responses as a function of temperature, relative humidity, and strain at three different excitation frequency ranges for a fixed geometric carbon nanotube-based multi-sensor. In these figures, the carbon-based nanotube multi-sensor utilized a serpentine pattern of four 150 micron long lines at a linewidth of 4 microns and a spacing of 2 microns. The fixed geometric carbon nanotube-based multi-sensor included a carbon nanotube mesh defined by 8 spray coated layers. Again, it should be apparent that the frequency range can be varied by the geometric configuration, e.g., serpentine compared to a patch pattern and dimensions thereof.

Figure 19:
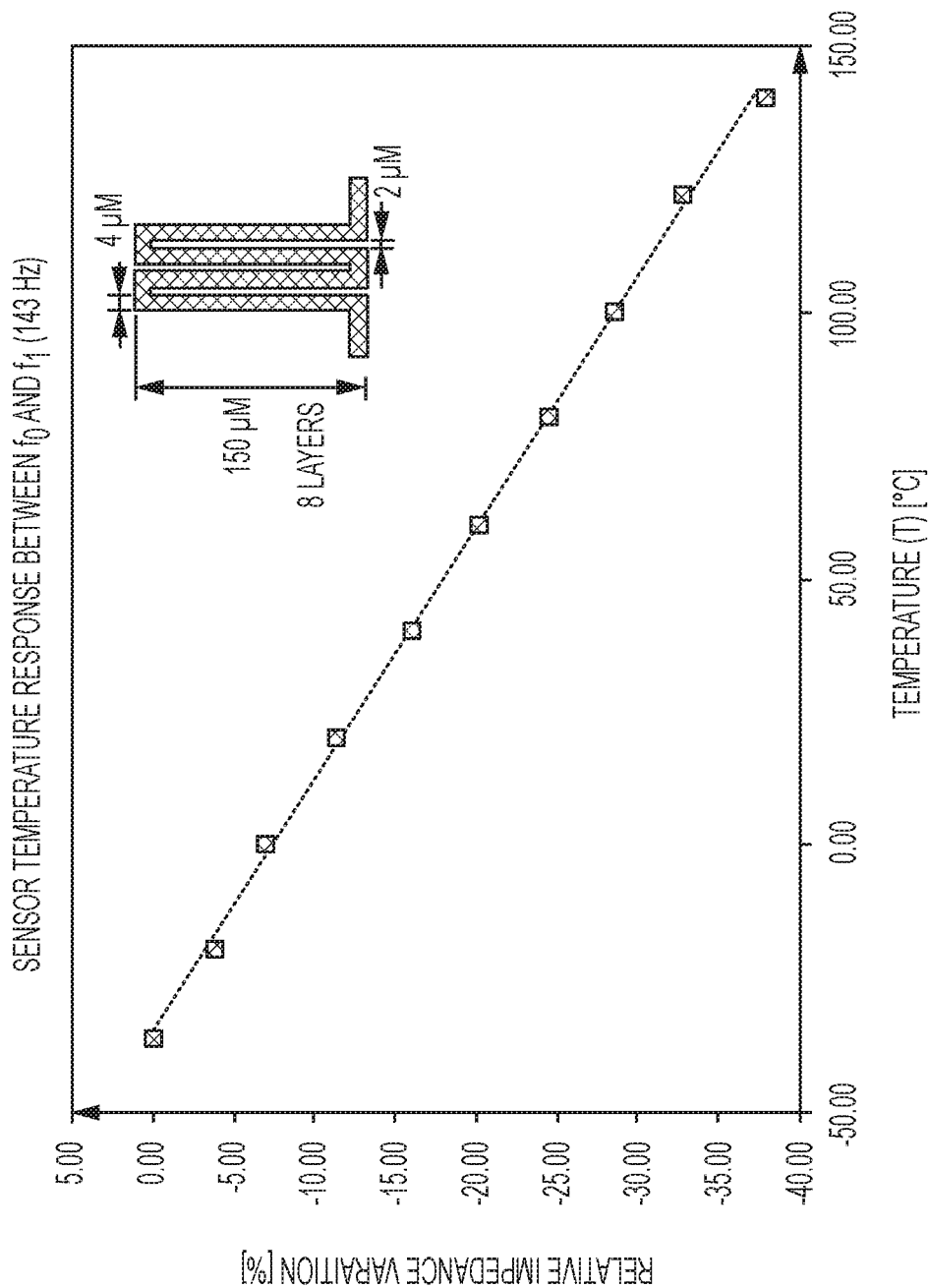
FIG. 19 graphically illustrates relative impedance variation as a function of temperature at a frequency of 143 Hz for the exemplary carbon nanotube-based multi-sensor of FIG. 18.

In FIG. 19, there is graphically shown relative impedance variation as a function of temperature response for the serpentine patterned carbon nanotube-based multi-sensor as described above at a defined frequency of 143 hertz (Hz). The relative impedance variation as a function of temperature response was highly sensitive at this excitation frequency and provided a substantially linear response.

Figure 20:
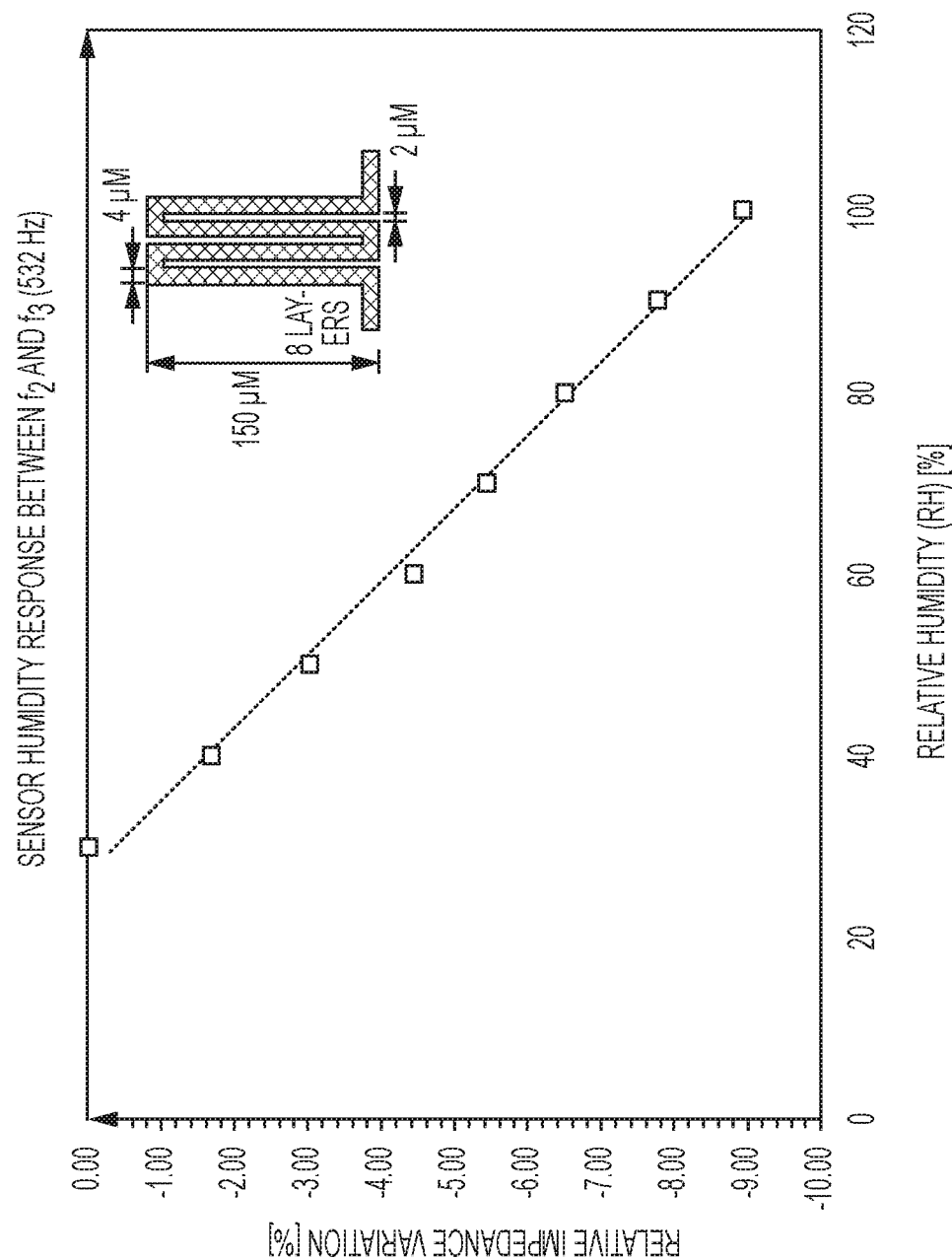
FIG. 20 graphically illustrates relative impedance variation as a function of relative humidity at a frequency of 532 Hz for the exemplary carbon nanotube-based multi-sensor of FIG. 18.

In FIG. 20, there is graphically shown relative impedance variation as a function of humidity response for the serpentine patterned carbon nanotube-based multi-sensor as described above at a defined frequency of 532 Hz, which is markedly higher than the frequency of 143 Hz (and corresponding range) used to effectively measure the relative impedance variation as a function of the temperature response.

Figure 21:
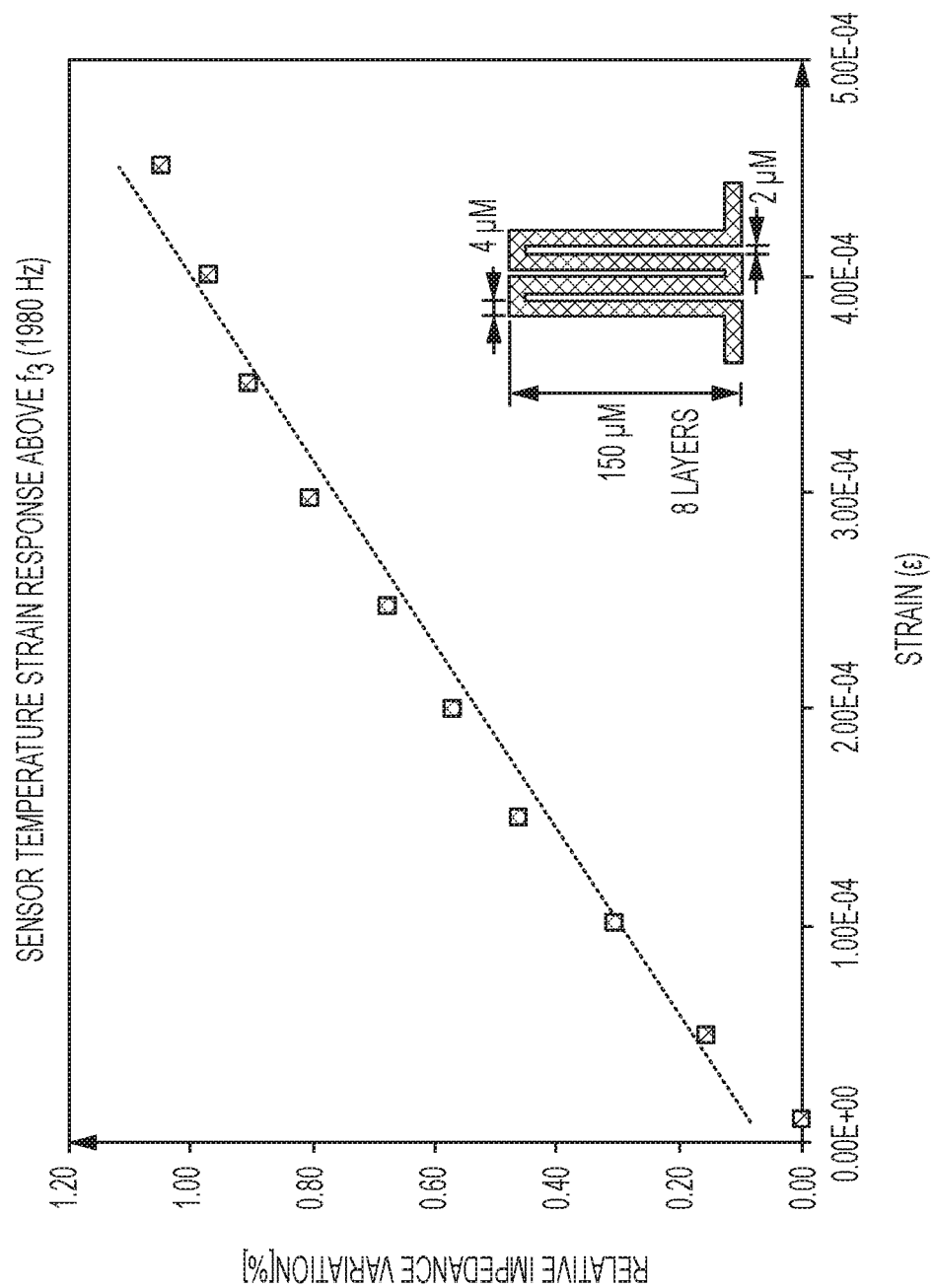
FIG. 21 graphically illustrates relative impedance variation as a function of strain at a frequency of 1980 Hz for the exemplary carbon nanotube-based multi-sensor of FIG. 18

In FIG. 21, there is graphically shown relative impedance variation as a function of strain response for the serpentine patterned carbon nanotube-based multi-sensor as described above at a defined frequency of 1980 Hz, which is markedly higher than the frequencies of 143 and 532 Hz (and accompanying ranges) used to monitor the temperature and the humidity responses.

Figure 22:
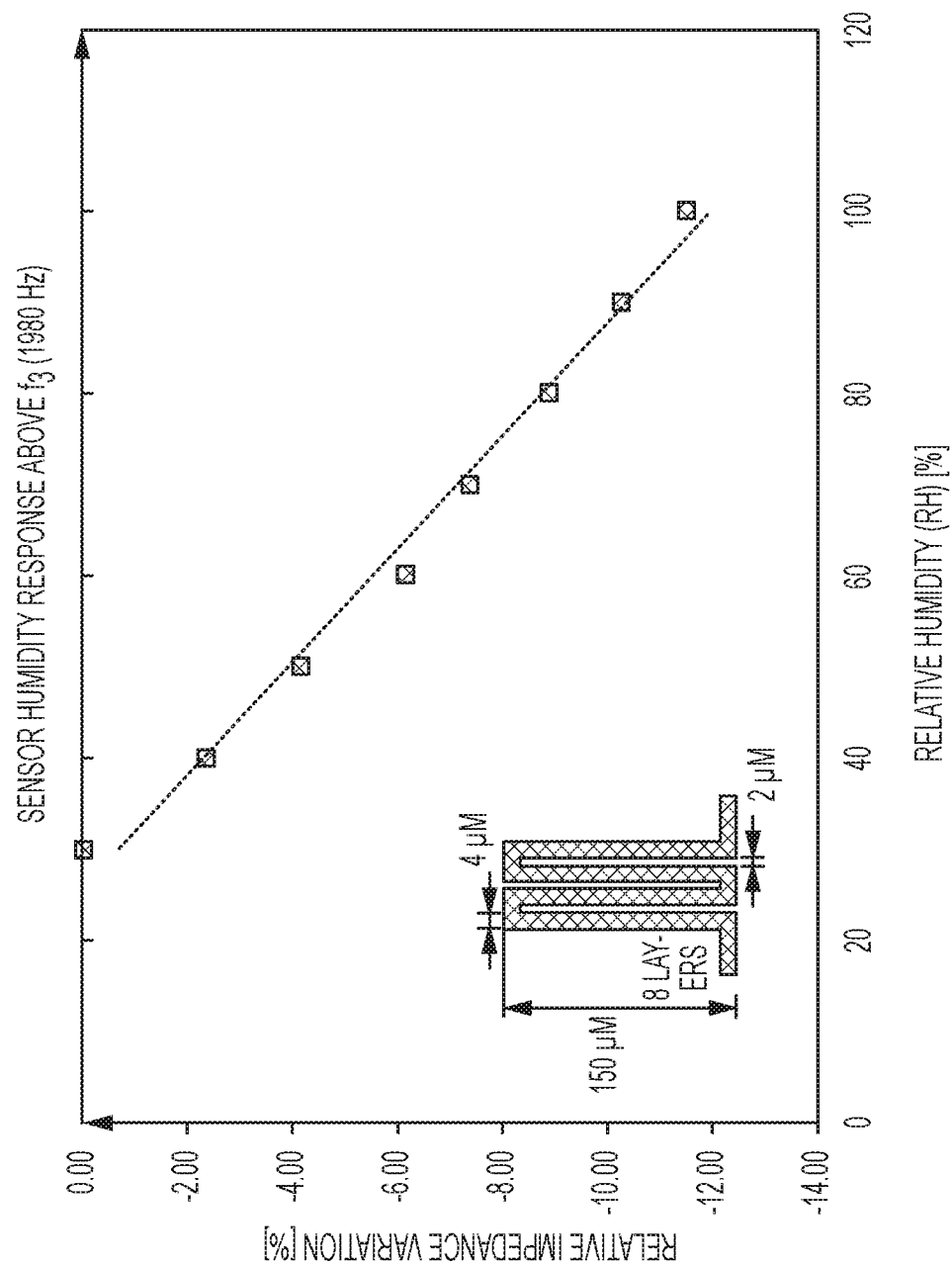
FIG. 22 graphically illustrates relative impedance variation as a function of humidity at a frequency of 1980 Hz for the exemplary carbon nanotube-based multi-sensor of FIG. 18.

FIG. 22 graphically shows the humidity response at the same frequency of 1980 Hz used to determine the strain response for the serpentine patterned carbon nanotube-based multi-sensor. Relative impedance variation as a function of the change in relative humidity was measured and is graphically presented. Because the strain and humidity responses are confounded at the same excitation frequency signal, signal treatment can be used to selectively isolate the impedance variation associated with the dependent variable, which in this case is the impedance variation associated with the strain response.

Figure 23:
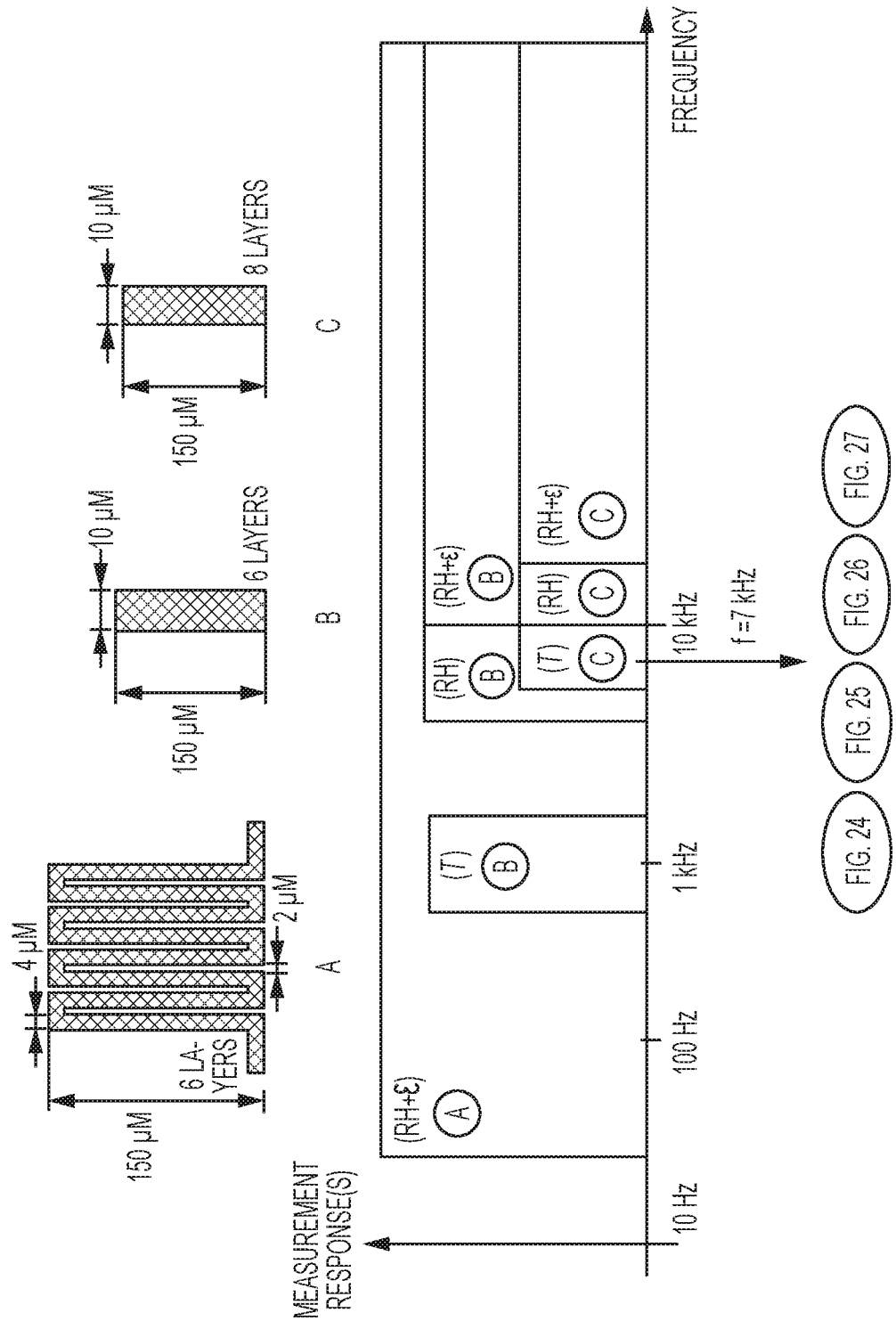
FIG. 23 graphically illustrates measurement response for various measurands as a function of frequency including the measurand response at 7 kHz for different geometric and resistive constructions of carbon nanotube-based multi-sensors in accordance with one or more embodiments of the present invention.

As shown in FIG. 23, in one more embodiments, variable geometry carbon nanotube-based multi-sensors can be used to measure temperature, strain and humidity responses at the same excitation frequency. As such, the chip would include multiple geometry carbon nanotube-based multi-sensors of varying geometric configuration to collectively provide the temperature, strain and humidity responses. By way of example, multiple carbon nanotube based sensors A, B, and C of different geometric configurations be configured with a different resistance are provided and the impedance variation as a function of a measurand was monitored at an excitation frequency signal of 7 kiloHertz (kHz). Sensor A includes a serpentine pattern and is the most resistive. The serpentine pattern includes eight 150 micron long lines at a linewidth of 4 microns and spacing of 2 microns. The carbon nanotube mesh defining the serpentine pattern included 6 spray coated layers. Sensors B and C were patch-patterned sensors having a length of 100 microns and a width of 10 microns. Sensor B had a mesh thickness defined by 6 spray coated layers whereas Sensor C being the least resistive sensor had a mesh thickness defined by 8 spray coated layers, i.e., a thicker carbon nanotube mesh layer.

Figure 24:
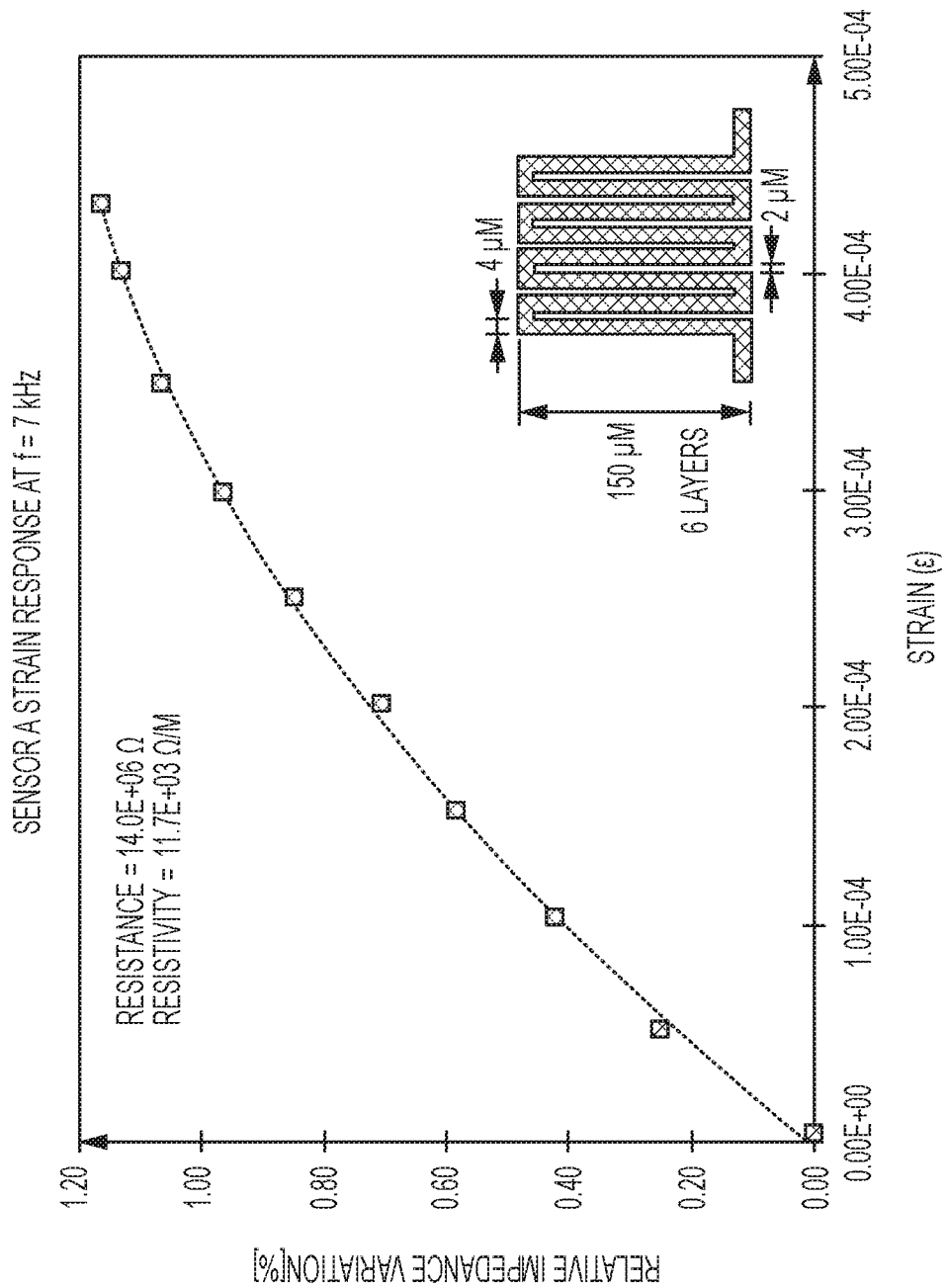
FIG. 24 graphically illustrates relative impedance variation as a function of strain at a frequency of 7 kHz for the serpentine patterned carbon nanotube-based multi-sensor A of FIG. 23.

FIG. 24 graphically shows the strain response as a function of relative impedance at the frequency of 7 kHz for the serpentine patterned carbon nanotube based multi-sensor A.

Figure 25:
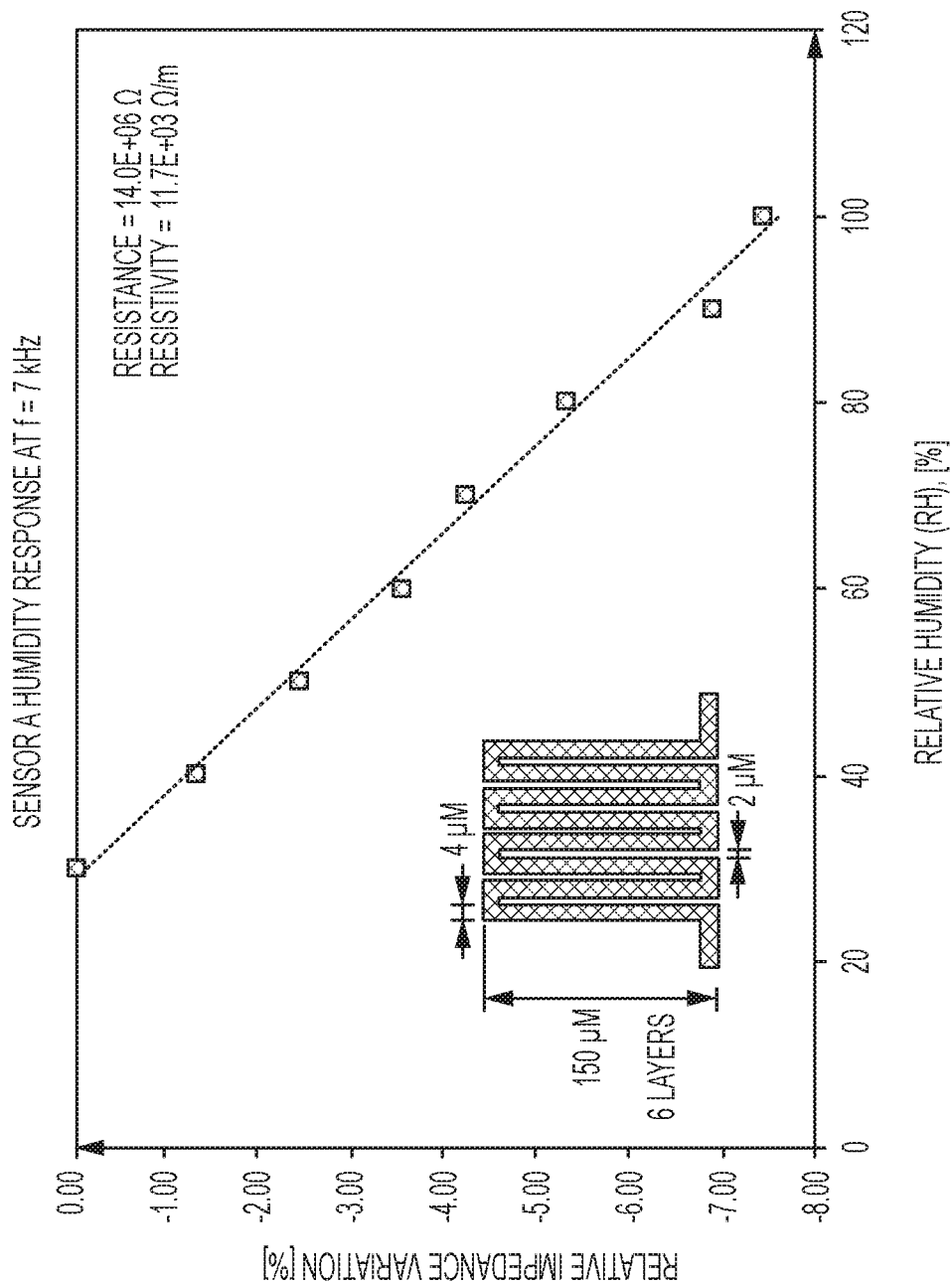
FIG. 25 graphically illustrates relative impedance variation as a function of humidity at a frequency of 7 kHz for the serpentine patterned carbon nanotube-based multi-sensor A of FIG. 23.

FIG. 25 graphically shows the humidity response as a function of relative impedance at the frequency of 7 kHz for the serpentine patterned carbon nanotube based multi-sensor A.

Figure 26:
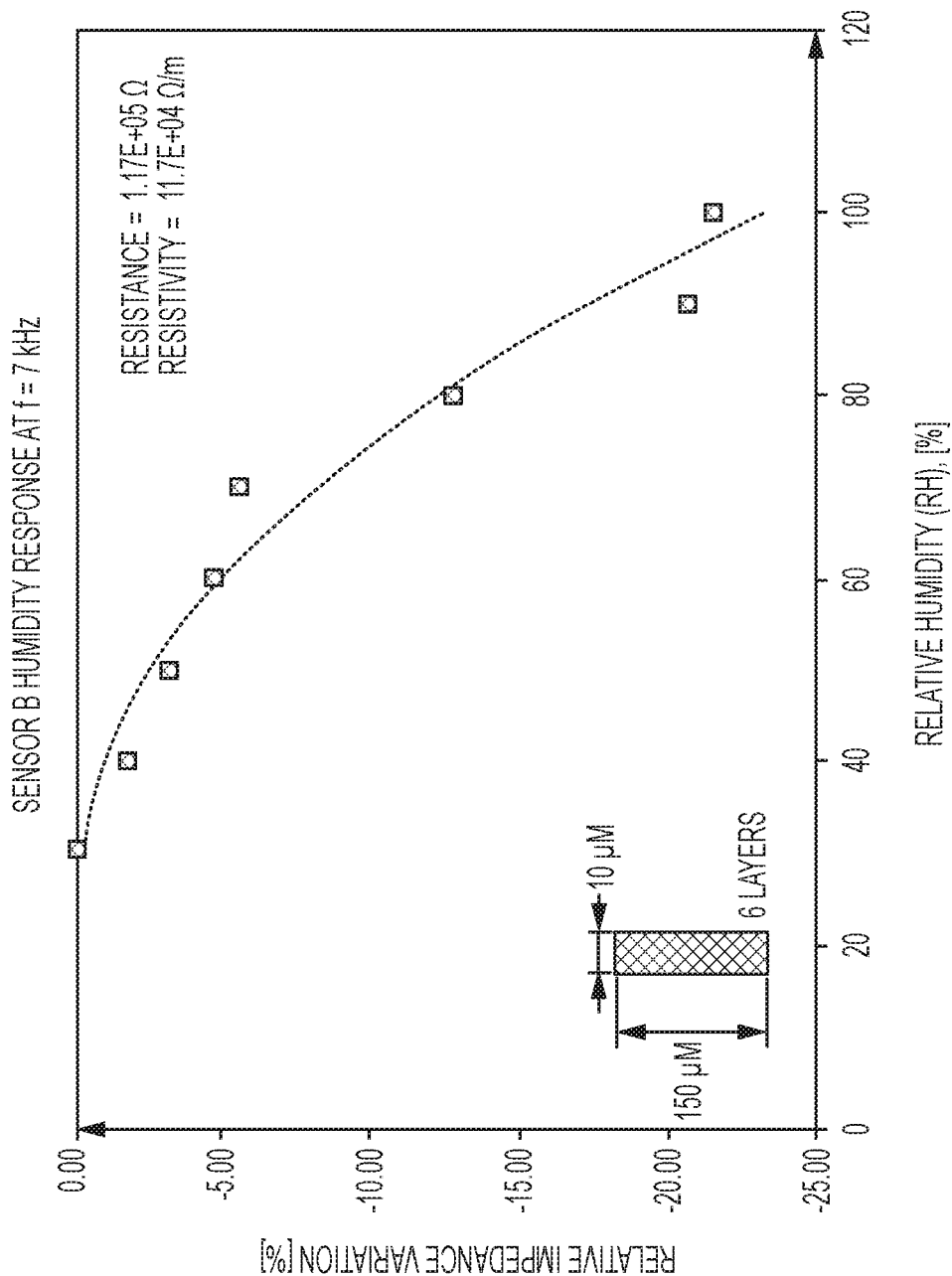
FIG. 26 graphically illustrates relative impedance variation as a function of humidity at a frequency of 7 kHz for the patch patterned carbon nanotube-based multi-sensor B of FIG. 23.

FIG. 26 graphically shows humidity response as a function of relative impedance at a frequency of 7 kHz for the first patch patterned carbon nanotube based multi-sensor B of lower resistance.

FIG. 27 graphically shows temperature response as a function of relative impedance at a frequency of 7 kHz for the second patch patterned carbon nanotube-based multi-sensor C having the lowest resistance of the three sensors.

The use of the three carbon nanotube-based multi-sensors provides measurand responses for temperature, humidity, and strain. By measuring the measurands at a frequency of 7 kHz, the humidity response obtained from sensor B can be used to isolate the strain response from the confounded humidity and strain response obtained by sensor A using a signal treatment algorithm, which is well within the skill of those in the art. Alternatively, an impermeable polymer matrix can be used with to encapsulate the carbon nanotubes and form a composite sensor material responding to strain only at the same 7 kHz frequency.

Relative to sensors of conventional technology that are configured to measure a single measurand, e.g., temperature, or humidity, or strain, the carbon nanotube-based multi-sensor of the present invention can measure multiple measurands at high sensitivities over relatively wide ranges. Table 1 provides comparative normalized sensitivities for different sensors of conventional technologies contrasted with the carbon nanotube-based multi-sensor of the present invention. The values reported for the sensors of conventional technology were provided from published literature.

TABLE 1

| TECHNOLOGY | Temperature $S_{T,n}$ [$10^{-3}$/K] | Humidity $S_{RH,n}$ [$10^{-3}$/RH] | Strain $S\varepsilon$ |
|---|---|---|---|
| Diodes | 2 to 3 | | |
| Polyimide | | 1.8 | |
| Si-based Piezoresistive | | | 150 to 200 |
| Foil-based | | | 2 to 4 |
| Carbon Nanotube-based Multi-Sensor | −1.5 to −2.5 | −0.9 to −4 | 10 to 50 |

The flow diagrams of the figures depicted herein are just examples. There may be many variations to these diagrams or the steps (or operations) described therein without departing from the spirit of the invention. For instance, the steps may be performed in a differing order, or steps may be added, deleted or modified. All of these variations are considered a part of the claimed invention.

It will be understood that when an element, such as a layer, is referred to as being "on" or "over" another element, it can be directly on the other element or intervening elements may also be present. In contrast, when an element is referred to as being "directly on" or "directly over" another element, there are no intervening elements present.

While the present invention has been particularly shown and described with respect to preferred embodiments, it will be understood by those skilled in the art that the foregoing and other changes in forms and details may be made without departing from the spirit and scope of the invention. It is therefore intended that the present invention is not be limited to the exact forms and details described and illustrated but fall within the scope of the appended claims.

What is claimed is:

1. A carbon nanotube-based multi-sensor for independently measuring temperature, strain, and relative humidity responses in a chip package comprising:
   a laminate substrate having a plurality of electrical circuits disposed therein;
   a chip having a first surface mounted on the laminate substrate and electrically connected to electrical circuits disposed in laminate substrate; and
   an underfill material disposed between the chip and the laminate substrate,
   wherein a selected one or both of the chip and the laminate substrate further comprises a passivation layer thereon,
   wherein the carbon nanotube-based multi-sensor is disposed on the passivation layer and comprises a carbon nanotube mesh pattern encapsulated in a moisture permeable polymer matrix with terminal ends exposed;
   electrodes coupled to the terminal ends, and
   a processor for treating a signal generated from the carbon nanotube-based multi-sensors when a voltage is applied to the electrodes, wherein the processor is configured to independently measure a variation in an electrical property at a defined frequency as a function of the temperature, strain and relative humidity.

2. The carbon nanotube based multi-sensor of claim 1, wherein the passivation layer is a photosensitive polyimide.

3. The carbon nanotube based multi-sensor of claim 1, wherein the variation in the electrical property comprises a variation of an impedance output by the carbon nanotube-based multi-sensor as a function of the temperature response, the strain response and/or the humidity response.

* * * * *